United States Patent [19]

Paszthory et al.

[11] 4,082,803
[45] Apr. 4, 1978

[54] PROCESS FOR PREPARING 4-CHLORO-2,5-DIMETHOXY ANILINE

[75] Inventors: Emmerich Paszthory, Hofheim, Taunus; Bernhard Mees, Konigstein, Taunus; Ernst Hille, Rossert, all of Germany

[73] Assignee: Hoechst Aktiengesellschaft, Frankfurt am Main, Germany

[21] Appl. No.: 634,634

[22] Filed: Nov. 24, 1975

[30] Foreign Application Priority Data

Nov. 25, 1974 Germany .............................. 2455704

[51] Int. Cl.$^2$ .............................................. C07C 93/14
[52] U.S. Cl. ................................................... 260/575
[58] Field of Search .......... 260/580, 575, 689, 141 AN

[56] References Cited

U.S. PATENT DOCUMENTS

| 1,679,211 | 7/1928 | Faber ..................................... 260/392 |
| 2,186,722 | 1/1940 | Gubelmann et al. .......... 260/141 AN |

FOREIGN PATENT DOCUMENTS

| 2,156,051 | 5/1973 | Germany .............................. 200/575 |
| 2,240,849 | 3/1974 | Germany .............................. 260/575 |

OTHER PUBLICATIONS

Frey, "College Chemistry," second edition, pp. 305–307 (1958).
Deming, "General Chemistry," fourth edition, pp. 378 & 379 (1935).
Fierz–David and Blangey, "Fundamental Processes of Dye Chemistry," fifth edition, p. 377 (1949).

Primary Examiner—Daniel E. Wyman
Assistant Examiner—John J. Doll
Attorney, Agent, or Firm—Curtis, Morris & Safford

[57] ABSTRACT

The catalytic hydrogenation of 4-chloro-2,5-dimethoxy nitrobenzene can be performed in water with a nickel catalyst if the average particle size is below 0.1 mm. The resulting aniline is reacted with diketene and the so-obtained N-acetoacetyl derivative is an azoic coupling component.

11 Claims, No Drawings

PROCESS FOR PREPARING 4-CHLORO-2,5-DIMETHOXY ANILINE

The present invention relates to a process for preparing 4-chloro-2,5-dimethoxy aniline.

4-Chloro-2,5-dimethoxy aniline is generally produced on an industrial scale by reducing 4-chloro-2,5-dimethoxy-nitrobenzene with iron according to the Bechamps method (cf. Bios Final Report 986, pages 79–81). According to that method, the nitro compound is dissolved in a technical-grade xylene mixture and reduced with iron; after elimination of the organic solvent, the amine is obtained with a moderate yield of a product having a brown to violet color. Better results are obtained following a catalytic reduction with hydrogen which, however, involves the risk of chlorine being split off. A process of that type is disclosed in German Patent No. 2,156,051. In that process, 4-chloro-2,5-dimethoxy nitrobenzene is dissolved in an aromatic solvent, and the solution is hydrogenated in the presence of a specifically prepared noble metal catalyst at elevated temperature. Although the yield and purity of the amine are very good with that process, the handling on an industrial scale is not quite simple since, instead of the commercial-type and cheap nickel catalysts, specifically poisened noble metal catalysts are used. Moreover, the use of aromatic solvents and the work-up thereof raise further economic and ecological problems.

The present invention now provides a process for preparing 4-chloro-2,5-dimethoxy aniline by catalytic reduction of 4-chloro-2,5-dimethoxy nitrobenzene, which comprises reducing 4-chloro-2,5-dimethoxy nitrobenzene having an average particle size of less than 100 microns in water and in the presence of a nickel catalyst.

The required fine division of the nitro compound can easily be achieved by grinding an aqueous suspension of the nitro compound in a colloidal mill (for example, a PUC mill) or in a toothed disk mill (for example, Supraton®). The necessary fine adjustment of the mill gear and the number of grinding operations can easily be determined by a preliminary test; generally, one grinding operation is sufficient.

The finely ground, aqueous suspension is placed in a usual hydrogenation autoclave, and a catalytic amount of nickel supported on an inorganic carrier material is added (for example Ruhrchemie nickel 55/5). The catalyst is preferably used in an amount of from about 0.01 to about 0.2 gram atom, especially about 0.03 to 0.1 gram atom, calculated on 1 mol of nitro compound. In addition, promoting agents as described in German Patent No. 2,240,849, such as disodium diborate, borax (disodium tetraborate), sodium dihydrogen phosphate or, preferably disodium hydrogen phosphate, as well as mixtures thereof, are added in catalytic amounts, preferably of from 0.03 to 0.1 mol, calculated on 1 mol of nitro compound. These promoting agents have a positive effect on the reaction and further bring about a certain stabilization of the pH-value, which may be important for the nitro compound since it may still contain minor amounts of nitric acid, due to the mode of preparation.

The reduction process can be carried out in the usual pressure apparatus, the reduction starting at 30° – 45° C approximately, as a function of the particle size of the nitro compound, the activity and concentration of the catalyst and the initial pressure of hydrogen. The temperature during the reduction is maintained at about 30° – 80° C, preferably at 35° – 70° C, in particular at 40° C to 65° C. The pressure ranges from about 10 to 100 atmsg., preferably from 20 to 50 atmsg., in particular from 40 to 50 atmsg. Higher pressures are possible but not necessary.

The reduction is preferably carried out by charging the aqueous suspension of the nitro compound into the autoclave, after the above fine division, with the nickel catalyst and optionally with the promoting agents, and after air has been expelled, e.g. by means of nitrogen, hydrogen is introduced under pressure, while stirring, and the mixture is heated. The desired reaction temperature is maintained by external cooling, and hydrogen is passed in until there is no more drop in pressure.

After the reduction is complete, the amine is separated by filtration, preferably under nitrogen and washed with water.

Owing to the fine division of the nitro compound preceding the reduction, the process of the present invention permits hydrogenation of 4-chloro-2,5-dimethoxy nitrobenzene into the corresponding aniline even in water under mild reduction conditions and with the use of commercial-type nickel catalysts, whereby an almost quantitative yield and a high degree of purity are obtained.

Another advantage of this process is the substantially lower reaction temperature as compared to that applied for the process of German Pat. No. 2,156,051.

4-Chloro-2,5-dimethoxy aniline in the form of its N-acetoacetyl compound is an important coupling component for the preparation of dyes and pigments.

The following Examples illustrate the invention, the parts and percentages being by weight unless stated otherwise.

EXAMPLE 1

In a colloidal mill (PUC), 2 kilograms of 4-chloro-2,5-dimethoxy nitrobenzene (of 100% strength) in the form of an about 80 – 85% aqueous slurry were ground with 4 liters of water until a particle size of 5 to 90 microns was reached. The suspension was suction-filtered on a laboratory-scale filter. The moist filter cake was stirred with 10 l of water and charged into a horizontally positioned hydrogenation autoclave having a 20 l-capacity. After addition of 50 g of a nickel catalyst (Ruhrchemie nickel 55/5), the autoclave was sealed and flushed with nitrogen. It was then pressurized with hydrogen up to a pressure of 40 atmsg. and heated with stirring. At about 38° C, reduction set in. Whenever the hydrogen pressure dropped below 20 atmsg., it was again raised to 40 atmsg. The temperature in the autoclave was limited to a maximum of 65° C by external cooling.

Hydrogen absorption was complete within 2 hours. Stirring was continued for half an hour, and pressure was then released. The hot suspension having a temperature of 50° – 60° C was pressed into a 50-l vessel provided with stirrer and was allowed to cool to room temperature. It was then suction-filtered and washed with water. The yield of isolated, dried amine amounted to 88% of the theoretical yield. By salting out, extracting or reusing the mother liquor, the yield could be further increased.

The base obtained was practically colorless and stable even in wet state with the catalyst.

Investigation by thin-layer chromatography confirmed the fact that no appreciable amount of chlorine had been split off.

EXAMPLE 2

In a colloidal mill (PUC), 100 kg of 4-chloro-2,5-dimethoxy nitrobenzene (100%) in the form of an about 80 – 85% aqueous slurry were ground with 200 l of water until the analysis of particle size showed an average particle size of 50 microns. A mixture of 200 g of disodium hydrogen phosphate and 200 g of monosodium dihydrogen phosphate was added to the suspension, whereupon the pH of the aqueous suspension was adjusted to 7.2. This suspension was then pumped into a horizontally positioned hydrogenation autoclave of 800 l capacity, and 3.5 kg of a nickel catalyst supported on an inorganic carrier material (Ruhrchemie nickel 55/5) were added. The autoclave was sealed and flushed with nitrogen. After the vessel had been pressurized with hydrogen up to a pressure of 50 atmsg., the temperature was raised, and reduction set in at 40° – 44° C. By external cooling and reducing the speed of the agitator, the temperature was maintained at 60° – 70° C, whereupon the reduction was complete within 2 hours. Hydrogen pressure was always kept at 50 atmsg. Stirring was continued for 30 minutes, the temperature was allowed to come to normal, and the suspension was filtered through a box-filter. The pH of the mother liquor was unaltered at 7.2. The yield of isolated, dried amine was 92%. By isolating further product from the mother liquor (extraction, concentration), the yield could be further increased to 98%.

Investigation by thin-layer chromatography confirmed the fact that only a minor amount of chlorine had been split off.

EXAMPLE 3

In a 3-cubic-meter steel vessel, 1,000 kg of 4-chloro-2,5-dimethoxy nitrobenzene (100%) in the form of an about 80 – 85% aqueous slurry were stirred with 2 cubic meters of water. The suspension was then pumped for 30 minutes through a toothed disk mill, whereupon the particle size of a sample of the suspension ranged from 1 to 50 microns. 2.5 Kilograms of disodium hydrogen phosphate and 2.5 kg of monosodium dihydrogen phosphate were added to the aqueous suspension, whereupon the pH was 7.2. After addition of 25 kg of a nickel catalyst (Ruhrchemie 55/5) the pH rose to 8.2. This suspension was heated to 45° C and charged into a vertical hydrogenation autoclave of 10 cubic meter capacity, provided with an agitator and gas inlet. 20 Kilograms of a surfactant based on nonylphenol polyglycol ether and 2 kg of a foam-depressing agent based on silicone oil were added to the suspension of 40° C, the autoclave was flushed with nitrogen and pressurized with 45 atmsg. of hydrogen. The reduction set in immediately, and the temperature was maintained at 65° C. The reaction took 2 hours. Stirring was then continued for 30 minutes, hydrogen pressure was released, and the suspension was pumped while hot into a steel vessel provided with a stirrer, which had a capacity of 10 cubic meters. After cooling to room temperature, the suspension was suction-filtered.

The yield of isolated, dried amine was 96% of the theoretical yield.

The pH-value of the mother liquor was 7.2.

We claim:

1. In a process for the preparation of 4-chloro-2,5-dimethoxy-aniline by catalytic hydrogenation of 4-chloro-2,5-dimethoxy nitrobenzene, the improvement comprising comminuting the nitro compound until the median particle size is below 100 $\mu$ and performing the hydrogenation with the comminuted nitro compound in the form of an aqueous slurry and in the presence of a nickel catalyst at a temperature of 30° to 80° C and a pressure of 10 to 100 atms.

2. A process as claimed in claim 1, wherein the temperature range is 40° to 65° C.

3. A process as claimed in claim 1, wherein the pressure range is 20 to 50 atms.

4. A process as claimed in claim 1, wherein the reaction medium contains a catalytic amount of a promotor selected from disodium diborate, disodium tetraborate, disodium hydrogeno phosphate, monosodium dihydrogeno phosphate and mixtures thereof.

5. A process as claimed in claim 4, wherein the promotor is a mixture of disodiumhydrogeno phosphate and monosodiumdihydrogeno phosphate.

6. A process as claimed in claim 4, wherein the promotor is a mixture of equal parts of weight of disodium dihydrogeno phosphate and monosodium dihydrogeno phosphate.

7. A process as claimed in claim 4, wherein 0.03 to 0.1 mol of promotor per mol of nitro compound is present.

8. A process as claimed in claim 1, wherein 0.01 to 0.2 g-atom of nickel catalyst per mol of nitro compound is present.

9. A process as claimed in claim 1, wherein 0.03 to 0.1 g-atom of nickel catalyst per mol of nitro compound is present.

10. In a process for the preparation of 4-chloro-2,5-dimethoxy-aniline by catalytic hydrogenation of 4-chloro-2,5-dimethoxy nitrobenzene, the improvement comprising comminuting the nitro compound until the median particle size is below 100 $\mu$ and performing the hydrogenation with the comminuted nitro compound in the form of an aqueous slurry and in the presence of a nickel catalyst at a temperature of 35° to 70° C. and a pressure of 10 to 100 atms.

11. In a process for the preparation of 4-chloro-2,5-dimethoxy-aniline by catalytic hydrogenation of 4-chloro-2,5-dimethoxy nitrobenzene, the improvement comprising comminuting the nitro compound until the median particle size is below 100 $\mu$ and performing the hydrogenation with the comminuted nitro compound in the form of an aqueous slurry, in the presence of a nickel catalyst and in the absence of a buffer at a temperature of 30° to 80° C. and a pressure of 10 to 100 atms.

* * * * *